United States Patent [19]

Harned

[11] 4,444,191

[45] Apr. 24, 1984

[54] COMFORT GARMENT

[76] Inventor: Marguerite J. Harned, 6301 Lincoln Ave., Evansville, Ind. 47715

[21] Appl. No.: 285,771

[22] Filed: Jul. 21, 1981

Related U.S. Application Data

[63] Continuation-in-part of Ser. No. 50,708, Jun. 21, 1979, abandoned.

[51] Int. Cl.³ ............................ A41C 3/02; A61F 5/02
[52] U.S. Cl. ............................................ 128/482; 2/45
[58] Field of Search ............... 128/482, 510, 494, 426, 128/488; 2/44, 45

[56] References Cited

U.S. PATENT DOCUMENTS

| | | | |
|---|---|---|---|
| 557,945 | 4/1896 | Beckett | 2/45 |
| 1,190,602 | 7/1916 | Sorkin | 2/45 |
| 1,231,011 | 6/1917 | Glasgow | 2/44 |

Primary Examiner—Doris L. Troutman
Attorney, Agent, or Firm—Warren D. Flackbert

[57] ABSTRACT

A comfort garment particularly characterized as a jogging support for the upper female anatomy which may assume various forms, as (1) a vest which includes the use of a nonelastic front panel and elastic straps attached thereto which combine to restrict upward and downward breast movement, a nonelastic back panel, and an expandable bottom and side panel which permits stretching action during jogging or like activity; (2) a similar form to that of (1) where, however, the entire garment is made from an elastic material and/or where the bottom and side and the back panels are unitary and expandable, or variations of the preceding; and, (3) a continuous wrapped unit serving the same restrictive breast movement functions, but maintained on the torso in halter/strap fashion.

In any instance, the garment is readily attired, being variously secured in position on the wearer in a sweater-like relationship and/or through the use of hooks, loop-pile type fastening material, ties, the aforesaid halter/-straps, and/or the like, and may serve as an undergarment or an outer garment. The particular material employed is chosen so as to avoid irritation during jogging use.

16 Claims, 11 Drawing Figures

U.S. Patent    Apr. 24, 1984    Sheet 1 of 3    4,444,191
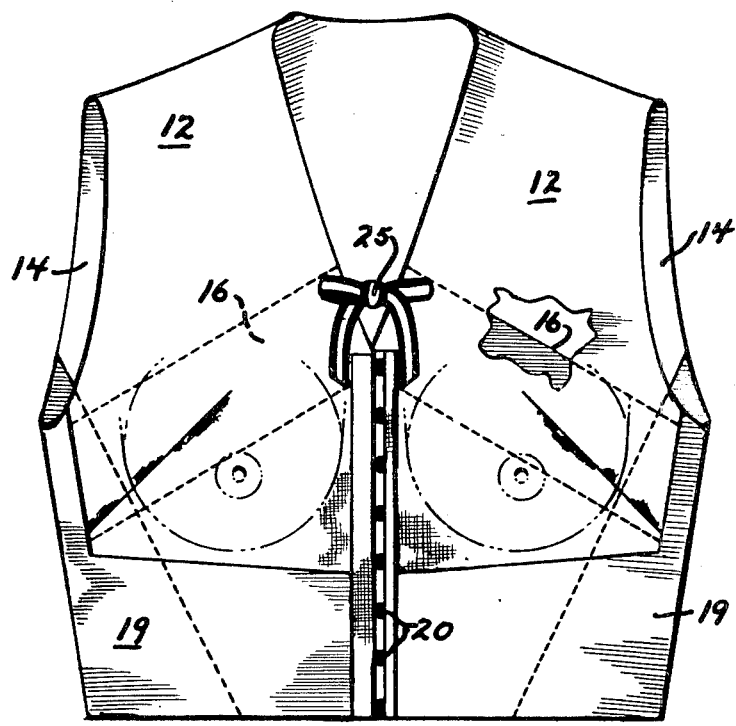
FIG. 1
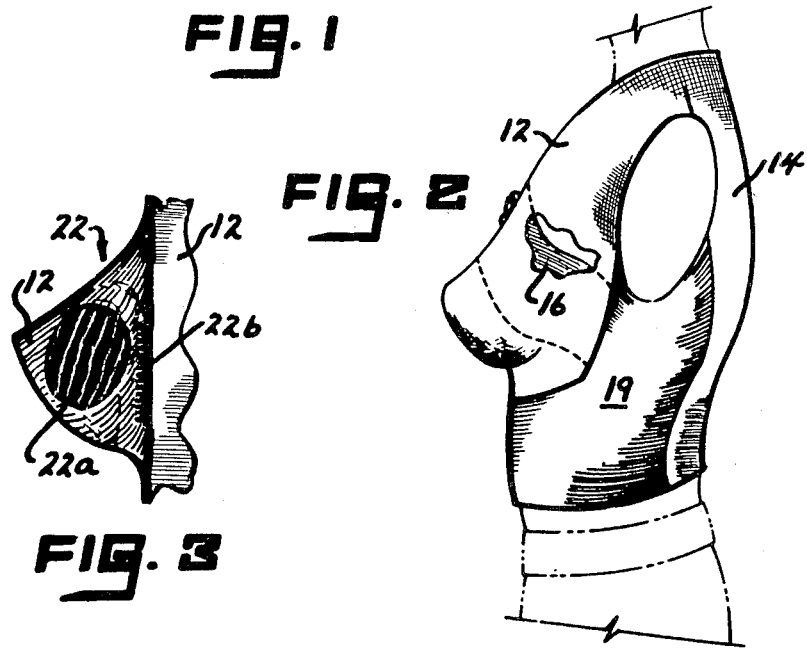
FIG. 2
FIG. 3

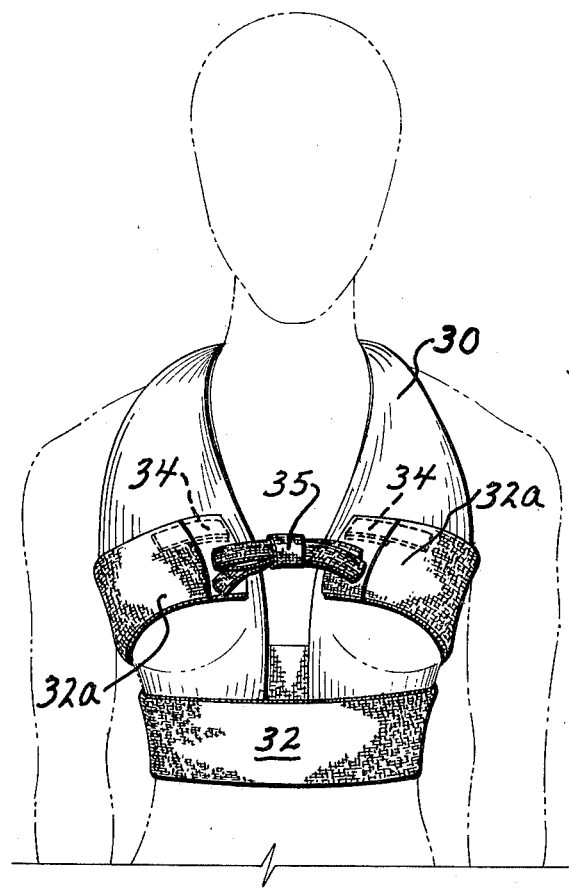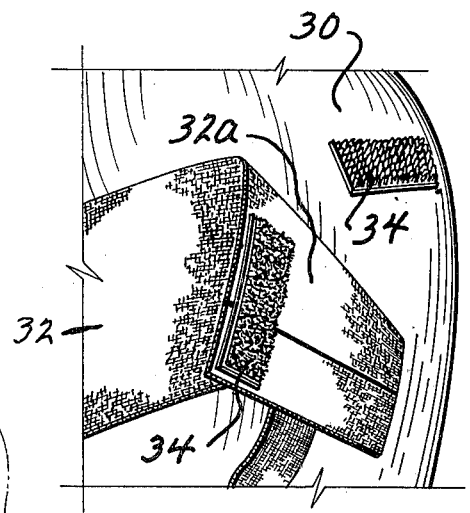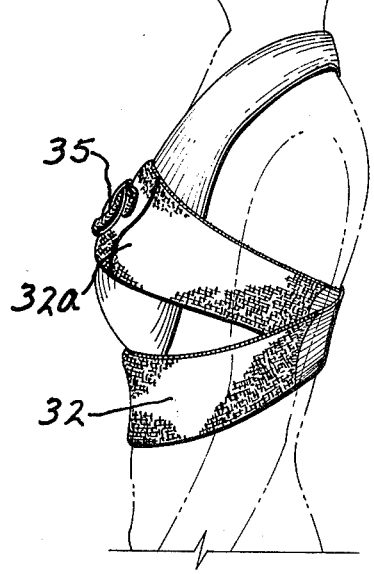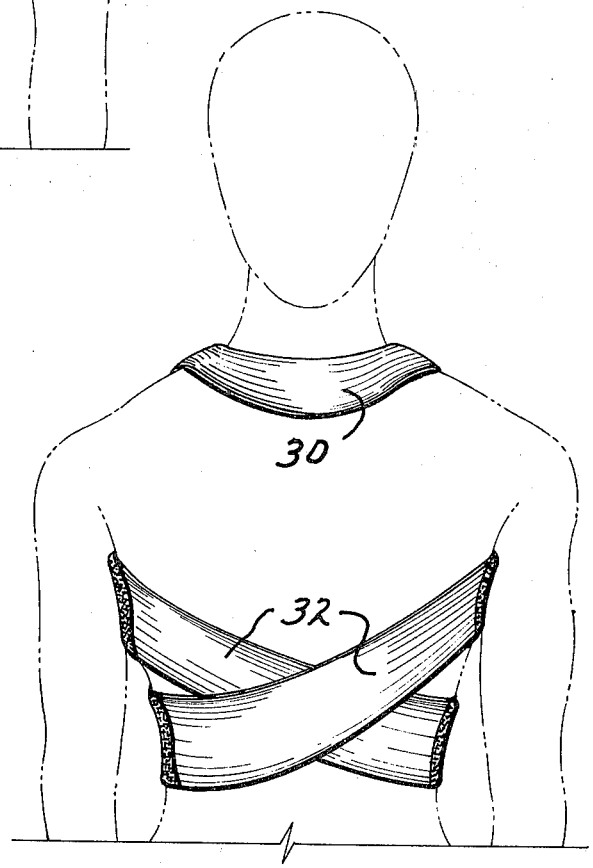
FIG. 4
FIG. 7
FIG. 5
FIG. 6

COMFORT GARMENT

The present application is a continuation-in-part application of Ser. No. 50,708, filed June 21, 1979, now abandoned with the same title and inventor.

As is known, jogging, for exercise/health and even, sometimes, social reasons, is widespread, extending to both males and females. In the latter instance, however, the jogging can cause an undesirable and possibly dangerous upward and downward stress effect in the breast area, particularly where the user employs no under support and/or where the individual is full figured. The preceding may result in disadvantages for the individual insofar as tissue pull or the like is concerned, and further create a tiring effect.

In contrast, the invention provides, in various forms, a comfort garment which permits running, jogging or like exercising for a female in a relaxed or untensed condition. The advantages afforded by the invention are accomplished by containing the upper part of the female torso, or breast area; in a relatively fixed condition, i.e. without the aforesaid undesired upward and downward motion during the jogging or like activity.

The latter is accomplished, basically, by a garment which is represented by three major portions, to-wit, a first portion encircling the mid-region of the wearer, a second portion slanting or angling over the upper areas of the female breasts, and a third portion, supported in a halter or strap fashion, which hugs, firms or otherwise restricts breast area movement and, at the same time, serves to maintain the second portion at the aforesaid slanted or angled relationship. The preceding summarizes the desired objectives afforded by any finished invention form.

In this connection, and by way of example, in one invention embodiment a vestlike garment is presented which includes (1) a front and a back panel, both made from a nonelastic material, which primarily, i.e. at the front panel, serves to limit and/or prevent undue vertical breast movement; (2) elastic straps, disposed on either the inner or the outer surface of the front panel to further restrict breast movement during jogging; and, (3) the provision of a bottom and side panel which is expandable to allow for the increased breathing occasioned during the physical activity.

As a variation of such embodiment, the entire garment may be made from an elastic or expandable material, attired as a sweater, or, at least the bottom, side and back panels are physically expandable. As a further variation, the aforesaid elastic straps might be made from nonelastic material, but secured to the garment in an elastic fashion to afford the restrictive vertical breast movement As a still further variation, the garment may be continuous in form, including a halter for positioning purposes on the torso. In this connection, and again referring to the aforenoted three major portions defining the invention, straps or a halter may be employed both to maintain the position of the slanted or angled upper breast overlying portion and, as well, the added restrictive function, i.e. against vertical breast movement, in combination with the portion encircling the wearer's mid-area.

In other words, the entire unit combines to fulfill an important need for female breast support during jogging, unlike any results achieved through the wearing of a conventional brassiere or sports bra. The invention is readily worn by the user, being in the form of an undergarment or an outer garment. The positioning or securing thereof may be accomplished, where appropriate, through a halter, straps, hooks, lacing, ties, or loop-pile type fastening material, or even as a sweater, depending upon particular design. The garment is easily styled for adoption to different female figures, is readily manufactured, and affords a pleasing appearance in addition to the highly important comfort feature.

In any event, a better understanding of the present invention will become more apparent from the following description, taken in conjunction with the accompanying drawing, wherein FIG. 1 is a view in front elevation showing a comfort garment formed in accordance with the teachings of the present invention;

FIG. 2 is a view in side elevation of the comfort garment of FIG. 1, showing the invention in use on a female form (in phantom);

FIG. 3 is an enlarged fragmentary view showing an alternative fastening arrangement for the garment, i.e. the use of loop-pile type material in contrast to the hooks of FIG. 1;

FIG. 4 is a view in front elevation of an alternative form of comfort garment in accordance with the teachings of the present invention;

FIG. 5 is a view in side elevation of the alternative form of comfort garment of FIG. 4;

FIG. 6 is a view in rear elevation, again with respect to the alternative form of comfort garment of FIGS. 4 and 5;

FIG. 7 is an enlarged fragmentary view showing a typical fastening arrangement for the FIGS. 4, 5, and 6 comfort garment embodiment;

Figure 2A:
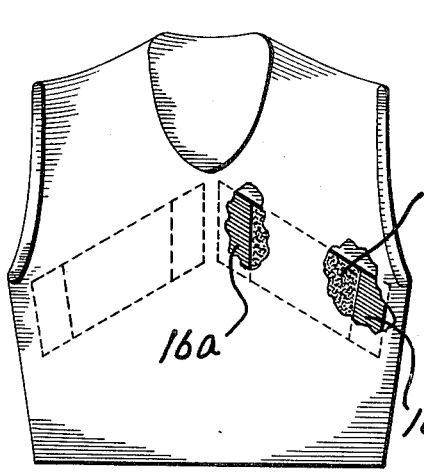
FIG. 2A is a view in front elevation showing an alternative form of comfort garment based on that of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications of the illustrated devices and such further applications of the principles of the invention as illustrated therein being contemplated as would normally occur to one skilled in the art to which the invention relates.

Referring now to the figures, and first particularly to FIGS. 1 and 2, the comfort garment of one embodiment of the invention is typically in the form of a vest which surrounds the upper torso, i.e. the breast area and the upper back, of the female figure, and includes separable front panels 12 secured, as by stitching, to a back panel 14 at the shoulder lines, where the front panels 12 and the back panel 14 are each made from a cotton material, or at least a nonelastic material, serving to provide a firmness or tightness which, insofar as the front panels 12 are concerned, restricts unwanted upward and downward movement of the breasts.

Additionally, and importantly, elastic straps 16 are disposed beneath (or, alternatively, above) sections of the front panel 12, overlying the upper portion of each breast, and serving supplemental restrictive movement purposes (see the broken line representations in FIGS. 1 and 2).

The comfort garment is completed by separable combined bottom and side panels 19 stitched to the front panels 12 and to the back panel 14 and extending upwardly to each arms eye. The bottom and side panels 19 are made from elastic material, such as commercially known "Spandex," to permit expansion or two-way stretch and, thereby, allow for mobility or "give" because of increased breathing occasioned by the jogging activity. In any event, the bottom and side panels 19 material affords stretchability, and, at the same time, should be of a type which does not cause skin irritation. In this connection, a common usage of the invention can be more as a vest over a conventional tee shirt, the latter serving undergarment purposes.

In order to properly secure and position the comfort garment, edges at the front thereof, i.e. along the separation of the sections of front panels 12 and the bottom panels 19, may include hooks 20 or other fastening means, including ties, laces, slide fasteners or the like.

In addition to the preceding, a bow 25 can be disposed in front of the comfort garment above the fastened edges of the separable panels, both for decorative purposes and for providing an increased pull for the desired tensioning effect.

Another fastening arrangement is disclosed in FIG. 3, in this instance employing loop-pile type material 22, one section 22a thereof cooperating in securing engagement with another section 22b thereof, respectively disposed on edges of adjacent panels. As a matter of clarification, the section 22a of loop-pile type material 22 is shown when a portion of the panel 12 edge is folded, i.e. to better illustrate the position thereof prior to fastening.

FIG. 2A illustrates an alternative embodiment of the invention comparable to that of FIGS. 1 and 2; however, in this instance, the comfort garment assumes the form of a pullover sweater, being completely made from elastic material, i.e. is not defined into front panels 12, bottom and side panels 19 and back panel 14. Importantly, the garment of FIG. 2A includes the aforedescribed elastic straps 16 in the same overlying relationship with respect to the upper portion of each breast.

Figure 2B:
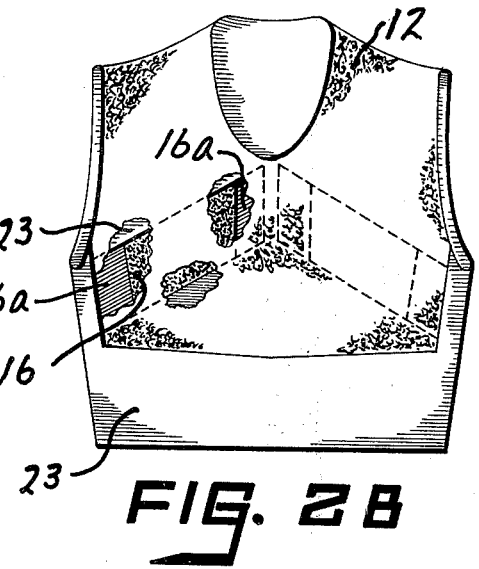
FIG. 2B is a view in front elevation showing still another alternative form of comfort garment, based on that of FIGS. 1 and 2A.

As to the presentation of FIG. 2B, a further variation of the garment (from that of FIGS. 1 and 2) is illustrated, being generally similar to the pullover form of FIG. 2A; however, the front panel 12 is not divided into sections, as in FIGS. 1 and 2. Instead, the front panel 12 is integral but made from a nonelastic material, where the bottom and side panels, together with the back panel, identified by reference numeral 23, are now all made from an elastic material. A modification is made in the embodiment of FIGS. 2A and 2B which are also adaptable to the showings of FIGS. 1 and 2, i.e. where the breast overlying straps 16 are made from a nonelastic material, but secured at the outer ends thereof to the remainder of the garment by elastic sections 16a. In other words, the vertical restrictive movement feature is still presented, but without each of the straps 16 being completely elastic in content.

In any event, the preceding should emphasize the versatility of the invention in that various forms and/or modifications could be presented which still satisfy the basic functions outlined hereabove. Further in this connection, such are again satisfied in FIGS. 4, 5, 6 and 7, directed to still another embodiment of the invention. In this alternative invention form, the comfort garment assumes a more or less continuous or one-piece arrangement fashioned to be attired in a wraparound-halter manner.

More specifically, the comfort garment is defined by a halter 30 positioned around the neck of the user and extending downwardly over each breast in a movement confining or restricting relationship, terminating, as by stitching, at a band 32 having a front portion which lodges against the mid-region of the user. As particularly evident in FIGS. 5 and 6, the band 32 continues in a wrapped relationship around the upper torso of the female, where free end portions 32a thereof are in an overlying or overlapping relationship with each of the wearer's breasts.

In order to assure positioning, and with particular reference to FIGS. 4 and 7, loop-pile assemblies 34 may be utilized to maintain the position of the free end portions 32a of the band 32 on a surface of the halter 30. Additional tensioning is afforded through the use of a decorative bow 35 which extends between the aforesaid free end portions 32a.

It should be evident, however, that the invention embodiment illustrated in FIGS. 4, 5 and 6 is further representative of the features underlying all described forms of the invention, i.e. the first portion disposed beneath the breast area at the mid-region of the user; the second portion overlying or overlapping the upper areas of each breast; and, the third portion which combines with the second portion to preclude unwanted vertical breast movement during jogging or like activity.

Figure 8:
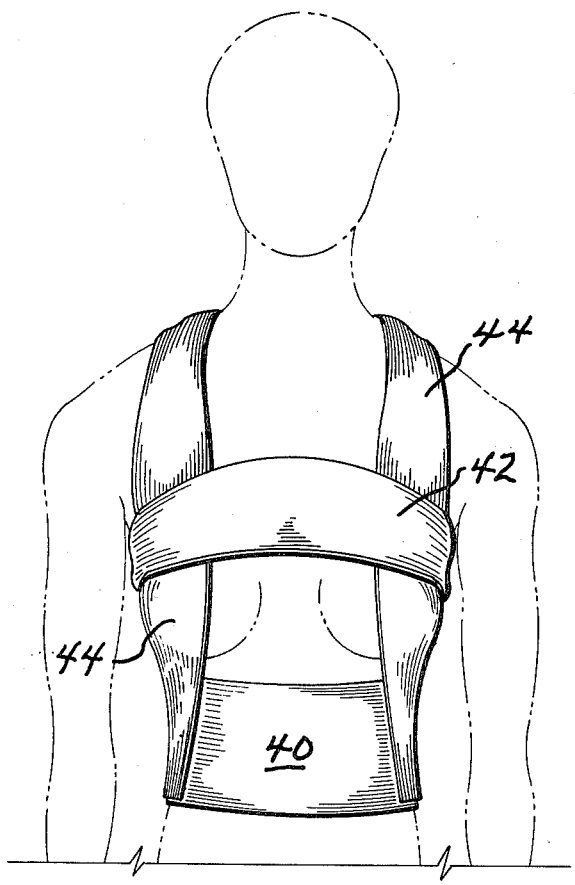
FIG. 8 is a view in front elevation showing a comfort garment unit illustrating the basic components underlying each of the preceding invention forms; and, FIG. 9 is a view in side elevation further showing the basic comfort garment component arrangement of FIG. 8.
Figure 9:
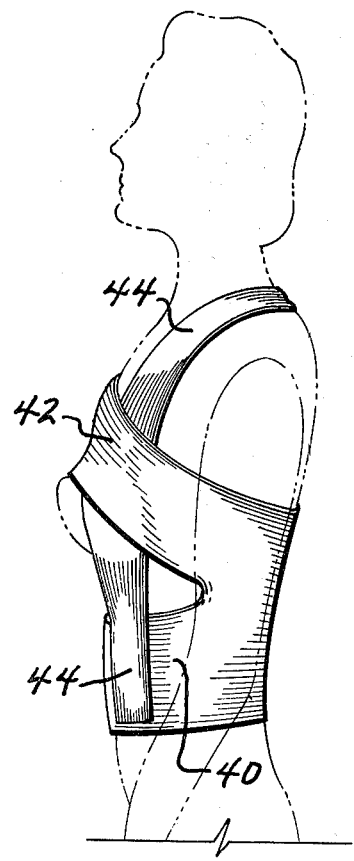

FIGS. 8 and 9 demonstrate, once again, the features enumerated in the preceding paragraph. In this instance, the invention is representatively disclosed. More specifically, first portion 40, disposed beneath the breast area, encircles the mid-region of the user, and integral therewith, although not necessarily, is the angled or upwardly slanted second portion 42. Third portion 44, which may pass or follow a path above or below the second portion 42, serves to assure the aforesaid upwardly angled or slanted relationship of the second portion 42.

The third portion 44, while illustrated as a halter, may also be presented as spaced apart over the shoulder straps. In any event, either the ends of the halter or the ends of the straps (not shown) are affixed in any desired manner to the first portion 40, such as by stitching, for example. The aforestated positive positioning of the second portion 42 by the third portion 44 may also be accomplished in a various number of approaches including, by way of example, and not shown, loop-pile fastening, hooks, snaps or the like.

Thus, basic function of the third portion 44 is twofold, namely, for positioning the second portion 42 and for overlying each of the breasts. In other words, the ultimate goal is the restriction or firming of the breasts into a stable non-movable condition, as by portion 44, jointly with the overlaying of each breast by the second portion 42, importantly serving to block vertical breast movement.

As should be evident from the preceding, the presented invention demonstrates various comfort garments to eliminate fatigue and like breast problems associated with jogging. Repetitiously, each invention form relates to the basic relationships variously described hereabove and particularized in the showing of FIGS. 8 and 9. In other words, and no matter how accomplished, the primary intent of the invention is the provision of the overlying breast portion suitably arranged with other supportive components, where various combinations of elastic or expandable material may be employed in accordance with design and/or appearance requirement.

Accordingly, the comfort garment described hereabove is susceptible to various changes within the spirit of the invention, as long as the basic features are presented in the ultimate apparel unit. Variations may include proportioning, the particular type of material employed, the manner of mechanical securing or fastening, or the like. Thus, the preceding should be considered illustrative and not as limiting the scope of the following claims:

I claim:

1. A comfort garment for the breast area of the torso of a female comprising a first portion encircling the region of the female below said breast area, a second portion extending upwardly and slantingly from said first portion in an overlapping holding down relationship with the upper portions of the breasts, and a third portion overlying the front of the breasts also in a movement restricting relationship.

2. The comfort garment of claim 1 where said second portion is expandable.

3. The comfort garment of claim 1 where said first portion and said second portion are expandable.

4. The comfort garment of claim 1 where said third portion extends upwardly from said first portion in a path including selective securing with said second portion and a supported relationship by a portion of said torso.

5. A comfort garment for the breast area of the upper torso of a female comprising a front portion cooperatively arranged with other portions to define an overall unit, and elastic confining straps disposed on said front portion in an overlying holding down relationship with the upper portions of the breasts, where the combination of said front portion and said elastic confining straps presents an arrangement restricting both upward and downward movement of said breasts, and where the remaining portions are selectively expandable for upper torso movement.

6. A comfort garment for the breast area of the upper torso of a female comprising a front panel, a back panel, and a bottom and side panel secured in an assembled relationship, and elastic confining straps disposed on said front panel in an overlying holding down relationship with the upper portions of the breasts, where the combination of said front panel and said elastic confining straps defines an arrangement restricting both upward and downward movement of said breasts, and where said bottom and side panel is expandable for diaphragm movement.

7. The comfort garment of claim 6 where said front panel and said bottom and side panel are vertically separable into sections, and where fastening means secure said sections of said front panel and said bottom and side panel in an operative relationship.

8. The comfort garment of claim 7 where said fastening means are hooks.

9. The comfort garment of claim 7 where said fastening means is a loop-pile arrangement.

10. The comfort garment of claim 9 where bow means connect and further secure said sections of said front panel and said bottom and side panel in an operative relationship.

11. A comfort garment for the breast area of the upper torso of a female comprising an elongated band having free ends, and a positioning member attached thereto supported by a portion of said torso, said elongated band encircling the mid-region of said torso and wrapping around said torso in an arrangement whereby said free ends are in an overlying and engaging vertical movement restricting relationship with the upper portions of the breasts, and means fastening said free ends in an operative relationship.

12. The comfort garment of claim 11 where said fastening means extend between said free ends of said elongated band and said positioning member.

13. The comfort garment of claim 11 where said fastening means includes a tensioning member extending between said free ends of said elongated band.

14. The comfort garment of claim 11 where said positioning member is a halter extending over and around the neck of said torso of the wearer.

15. The comfort garment of claim 11 where said positioning means are straps overlying the shoulder areas of said torso of the wearer.

16. The comfort garment of claim 11 where said elongated band is selectively expandable.

* * * * *